US 7,196,148 B2

(12) United States Patent
Vaughan

(10) Patent No.: US 7,196,148 B2
(45) Date of Patent: *Mar. 27, 2007

(54) CATIONIC CATALYST SYSTEM

(75) Inventor: George A. Vaughan, Houston, TX (US)

(73) Assignee: Exxon Mobil Chemical Patents Inc., Houston, TX (US)

( * ) Notice: Subject to any disclaimer, the term of this patent is extended or adjusted under 35 U.S.C. 154(b) by 102 days.

This patent is subject to a terminal disclaimer.

(21) Appl. No.: 10/399,736

(22) PCT Filed: Oct. 25, 2001

(86) PCT No.: PCT/US01/47697

§ 371 (c)(1),
(2), (4) Date: Apr. 18, 2003

(87) PCT Pub. No.: WO02/059157

PCT Pub. Date: Aug. 1, 2002

(65) Prior Publication Data

US 2004/0024234 A1    Feb. 5, 2004

(51) Int. Cl.
*C08F 4/6392*    (2006.01)
*C08F 4/70*    (2006.01)

(52) U.S. Cl. .................. 526/161; 526/160; 526/172; 502/162; 502/167; 502/117; 502/152; 502/155

(58) Field of Classification Search ............... 502/117, 502/162, 167, 155, 152; 526/161, 172, 160
See application file for complete search history.

(56) References Cited

U.S. PATENT DOCUMENTS

| | | | |
|---|---|---|---|
| 5,064,802 A | 11/1991 | Stevens et al. | |
| 5,312,881 A | 5/1994 | Marks et al. | |
| 5,318,935 A | 6/1994 | Canich et al. | |
| 5,455,317 A | 10/1995 | Marks et al. | |
| 5,464,906 A | 11/1995 | Patton et al. | |
| 5,563,219 A | 10/1996 | Yasuda et al. | |
| 5,707,913 A | 1/1998 | Schlund et al. | |
| 6,559,091 B1* | 5/2003 | Moody et al. | 502/167 |
| 2003/0100441 A1* | 5/2003 | Ittel et al. | 502/103 |
| 2004/0033891 A1* | 2/2004 | Hessen et al. | 502/150 |

FOREIGN PATENT DOCUMENTS

| | | |
|---|---|---|
| EP | 0 765 888 A2 | 4/1997 |
| WO | WO 96/13529 | 5/1996 |
| WO | WO 97/23493 | 7/1997 |
| WO | WO 97/42228 | 11/1997 |

OTHER PUBLICATIONS

U.S. Appl. No. 60/172,261.*
Bylikin et al., J. Chem. Soc., Dalton Trans., 2001, pp. 170-180.*
Booij, et al., "On the synthesis of monopentamethylcyclopentadienyl derivatives of yttrium, lnthanum, and cerium", *Journal of Organometallic Chemistry*, 364 (1989), pp. 79-86.
Hajela, et al., "Competitive Chain Transfer by β-Hydrogen and β-Methyl Elimination for the Model Ziegler-Natta Olefin Polymerization System $[Me_2Si(\eta^5-C_5Me_4)_2]Sc\{CH_2CH(CH_3)_2\}(PMe_3)^+$", *Organometallics*, vol. 13, 1994, pp. 1147-1154.
Scollard, et al., "Polymerization of α-Olefins by Chelating Diamide Complexes of Titanium", *Macromolecules*, vol. 29, 1996, pp. 5241-5243.
Coughlin, et al., "Iso-Specific Ziegler-Natta Polymerization of α-Olefins with a Single-Component Organoyttrium Catalyst", *J. Am. Chem. Soc.*, vol. 114, 1992, pp. 7606-7607.
Shapiro, et al., "$[\{(\eta^3-C_5Me_4)Me_2Si(\eta^1-NCMe_3)\}(PMe_3)ScH]_2$: A Unique Example of a Single-Component α-Olefin Polymerization Catalyst", *Organometallics*, vol. 9, 1990, pp. 867-869.
Piers, et al., "α'Agostic' Assistance in Ziegler-Natta Polymerization of Olefins. Deuterium Isotopic Perturbation of Stereochemistry Indicating Coordination of an α C-H Bond in Chain Propagation", *J. Am. Chem. Soc.*, vol. 112, 1990, pp. 9406-9407.
Shapiro, et al., "Model Ziegler-Natta α-Olefin Polymerization Catalysts Derived from $[\{(\eta 5-C_5Me_4)SiMe_2(\eta^1-NCMe_3)\}(PMe_3)Sc(\mu_2-H)]_2$ and $[\{(\eta^5-C_5Me_4)SiMe_2(\eta^1-NCMe_3)\}Sc(\mu_2- CH_2CH_2CH_3)]_2$. Synthesis, Structures, and Kinetic and Equilibrium Investigations of the Catalytically Active Species in Solution", *J. Am. Chem. Soc.*, vol. 116, 1994, pp. 4623-4640.
Britta, et al., "Phenoxyl radical complexes of gallium, scandium, iron and manganese", *Chem. Eur. J.*, 1997, 3, No. 2, pp. 308-319.
Schnepf, et al., "Resonance Raman Spectroscopic Study of Phenoxyl Radical Complexes", *J. Am. Chem. Soc.*, vol. 120, 1998, pp. 2352-2364.
Bylikin, et al., "New main-group and early transition-metal complexes of mono-pendant arm triazacyclononane ligands", *J. Chem Soc., Dalton Trans* (2001), (2), pp. 170-180.
Wang, et al., "Coordination Polymerization of Ethylene by Single-Component Rhodium Catalysts in Protic Solvents", *J. Am. Chem. Soc.*, vol. 115, 1993, pp. 6999-7000.

* cited by examiner

*Primary Examiner*—Roberto Rabago
(74) *Attorney, Agent, or Firm*—Catherine L. Bell

(57) ABSTRACT

A 3+ metal complex for coordination polymerization of olefins is disclosed. The precursor metal complex is stabilized by a anionic multidentate ligand and at least two monoanionic ligands. The multidentate ligand and the transition metal form a metallocycle having at least five primary atoms, counting any π-bound cyclopentadienyl group in the metallocycle as two primary atoms. Olefin polymerization is exemplified.

7 Claims, No Drawings

CATIONIC CATALYST SYSTEM

FIELD

This invention relates to certain transition metal compounds containing a neutral polyhaptate ligand and a tethered or bulky anionic ligand with the transition metal preferably in the +3-oxidation state, and to a catalyst system comprising those compounds and optionally alumoxane, modified alumoxane, or non-coordinating anion activator, Lewis acid, or the like to form active catalyst species, preferably cationic, for the production of polyolefins such as polyethylene, polypropylene and alpha-olefin copolymers of ethylene and propylene having a high molecular weight.

BACKGROUND

It is well known to those skilled in the art that the polyhaptate nature of the cyclopentadienyl anion confers unique properties to polymerization catalysts derived therefrom such as stability toward ligand loss or exchange and occupation of several coordination sites on the metal center (e.g. three in the pseudo octahedral environment of CpCr $(CO)_3$) so that its coordination environment is controlled and well defined. This results in more single sited behavior of the catalyst systems relative to e.g. Ziegler-Natta $TiCl_4$/aluminum alkyl based systems, conferring all the benefits of single sited nature such as narrow distributions of molecular weight and comonomer and "tunability" of catalyst performance by variations in the polyhaptate ligand. For the purposes of the description of the invention in this section, "polyhaptate" is taken to mean a ligand that contacts a metal center in a bonding interaction through more than one atom, whether the polyhaptate ligand has a formal charge or is neutral. Thus the "neutral polyhaptate ligand" will contact the transition metal through at least two atoms which are not considered to have a localized, negative charge or a negative charge delocalized between them as in cyclopentadienide. Similarly, the "tethered or bulky monoanionic ligand" may be polyhaptate and will have a negative charge. It is further well known that addition of a second cyclopentadienyl ligand or a tethered anionic ligand to form biscyclopentadienyl complexes or e.g. dimethylsilylbridged cyclopentadienylamide (so called "constrained geometry") complexes results in improved performance relative to the more open, less sterically locked complexes such as $CpZrCl_3$, $CpZr(OR)_3$, or $CpTiCl_3$ and the like which generally show broader comonomer and molecular weight distributions associated with a multi-sited nature as well as lower activity. Thus the favored "well defined ligand sets" contain a polyhaptate ligand with a bridged monohaptate ligand or an optionally bridged second polyhaptate ligand. Generally in the art the preferred "well defined" catalysts systems use: polyhaptate dianionic ligand sets such as biscyclopentadienyl or bridged cyclopentadienylamido; they use Group 4 metals, especially Zr and Ti; the metals are in their highest oxidation state and are accepted to be cationic with one alkyl or polymer ligand for chain propagation and one open coordination site for olefin coordination prior to or concurrent with insertion; there are no other labile ligands e.g. chloride, alkoxide, carboxylate left on the metal; and a weakly or "non" coordinating anion balances charge. Some nickel-based systems recently reported both by Johnson at DuPont and Grubbs at Caltech are believed effective in the neutral form. In order to maintain the favorable coordination environment of the polyhaptate dianionic ligand sets while using transition metals other than Group 4, many have substituted one or both anionic cyclopentadienyl (Cp) or amido ligands with isoelectronic dianionic analogues. Thus Bazan's substitution of one Cp with a dianionic borrole $(C_4H_4BR^{2-})$ allows synthesis of Group 5 complexes in their highest oxidation state while preserving as many of the characteristics of the preferred "well defined ligand set" systems as possible. Similarly Gibson's substitution of two Cps with dianionic imido ligands yields chromium catalysts in their highest oxidation state. This strategy only allows the preparation of cationic catalysts from Groups 5 or higher, while neutral versions could be made for Group 4 or higher. Much less common has been the strategy to maintain one polyhaptate anionic ligand such as Cp and use a tethered neutral ligand to create the "well defined" ligand set. This approach allows the preparation of Group 3 analogues and catalysts from any group in the 3+ oxidation state or lower.

We are not aware of anyone using the approach of substituting the polyhaptate anionic ligand such as Cp with a polyhaptate neutral ligand and an anionic ligand, both selected to provide a "well defined" i.e. relatively non labile ligand set. This has the advantage of allowing a valence to offset the anionic propagating polymer chain and a valence to create a positive charge with an open coordination site if desired. Many polyhaptate ligands offer far more structural diversity and ease of synthesis than e.g. substituted Cps, e.g. hexahydrotriazines made from the condensation of formaldehyde with amines. This could allow the use of any transition metal with a readily accessible 3+ oxidation state such as Sc, Y, La, lanthamides and actinides, V, Nb, Cr, Co, etc. It is this concept that is embodied in the present invention. It is not anticipated that the active species must be cationic or must be in a 3+ oxidation state because those skilled in the art will know that neutral complexes or lower oxidation states may prove competent for catalysts, or that the exact nature of the active species may be difficult to prove when it is derived e.g. from a lower oxidation state starting material. Rather, the catalysts of the invention will be distinguished in that they contain at least a neutral polyhaptate ligand and an anionic ligand, for which said anionic ligand will be either bridged to the polyhaptate ligand or be of a size to afford some degree of steric protection against its substitution.

Neutral scandium compounds having two univalent ligands or a bidentate, divalent ligand are known from Shapiro et al., Organometallics, vol. 9, pp. 867–869 (1990); Piers et al., J. Am. Chem. Soc., vol. 112, pp. 9406–9407 (1990); Shapiro et al., J. Am. Chem. Soc., vol. 116, pp. 4623–4640 (1994); Hajela et al., Organometallics, vol. 13, pp. 1147–1154 (1994); and U.S. Pat. No. 5,563,219 to Yasuda et al. Similar yttrium, lanthanum and cerium complexes are disclosed in Booij et al., Journal of Organometallic Chemistry, vol. 364, pp. 79–86 (1989) and Coughlin et al., J. Am. Chem. Soc., vol. 114, pp. 7606–7607 (1992). Polymerization with a metal scandium complex having a bidentate, divalent ligand using a non-ionizing cocatalyst is known from U.S. Pat. No. 5,464,906 to Patton et al.

Group-3-10 metallocyclic catalyst complexes are described in U.S. Pat. Nos. 5,312,881 and 5,455,317, both to Marks et al.; U.S. Pat. No. 5,064,802 to Stevens et al.; and EP 0 765 888 A2.

Polymerization of olefins with cationic Group-4 metal complexes is illustrated in WO 96/13529 and WO 97/42228. Boratabenzene complexes of Group-3-5 metals are disclosed in WO 97/23493.

Amidinato complexes of Group-3-6 metals are disclosed in U.S. Pat. No. 5,707,913 to Schlund et al. Group 4 bisamido catalysts are disclosed in U.S. Pat. No. 5,318,935 to Canich, et al., and related multidentate bisarylamido catalysts are disclosed by D. H. McConville, et al, Macromolecules 1996, 29, 5241–5243.

Monoanionic and Polyhaptate Ligands for Catalysis.

While replacing Cp⁻ ligands with dianionic formal 6 electron donors has been known to give active catalysts if the metal identity or number of labile ligands are adjusted to maintain an "isoelectronic" state, the practice of using 6 electron neutral donor ligands has received little attention. We believe that the ligand set defined by a neutral polyhaptate donor optionally bridged to a monoanionic donor are suited to stabilize lanthamides, actinides, and group 3 metals, $Ti^{III}$, $V^{III}$, $Cr^{III}$, $Fe^{III}$, and $Co^{III}$ in configurations with two labile ligands such as chloride in such a way as to promote polymerization activity with a suitable activator. It is depicted as follows:

(where T=optional bridge, L=polyhaptate neutral donor ligand, E=monoanionic ligand, M=a metal, preferably in the 3+ oxidation state, Q=labile ligands such as chloride, methyl, etc., L'=neutral donor ligands such as ethers, phosphines, amines, LiCl, olefins, cyclooctadiene). Versions with a single Q ligand for $Fe^{II}$ etc. could readily be envisioned.

SUMMARY

The present invention is directed to a catalyst system for olefin polymerization. The catalyst system contains a formally +3 cationic metal center stabilized by a neutral 6-electron donor and a monoanionic donor optionally bridged to the multidentate neutral ligand. The metal can be any +3 actinide, lanthamide, or Group-3, -4, -5, -6, -7, -8, -9 transition metal, or +3 main group metal.

In one embodiment, the multidentate ligand, A, has the formula LTE wherein L is a bulky neutral π-donating ligand, preferably containing at least two Group-15-16 atoms, most preferably at least three. T is a covalent bridging group containing a Group-13, -14, or -15 element. E is an anionic ligand containing a Group-14-16 element, including πt-donating hydrocarbyl and heterohydrocarbyl ligands, substituted amido or phosphido ligands, oxygen or sulfur, or other ligands or atoms covalently bound to T. Alternatively, E is $JR'_z$ where J represents an element from Group-15 or -16. When J is a Group-15 element, z=2, and when J is a Group-16 element, z=1. Finally, each R' is independently selected from suitable organic ligands as defined below.

In a further embodiment, a polymerization process according to the present invention (invention polymerization process), such as the polymerization or copolymerization of olefins, comprises the steps of activating (ionizing) the +3 metal component to a cation (the catalyst) and contacting it with suitable feedstocks. These feedstocks contain predominately one monomer for homopolymerization; they contain monomer mixtures for copolymerization. Suitable feedstocks are made up of any desired mixture of ethylene, $C_3$–$C_{20}$ α-olefins, $C_5$–$C_{20}$ diolefins, acetylenically unsaturated monomers, or other unsaturated monomers. The catalyst can optionally be dissolved, suspended, or fluidized in a suitable liquid or gaseous polymerization diluent. The catalyst is activated with alumoxanes, modified alumoxanes, non-coordinating anion activators, Lewis acids or the like, (alone or in combination), with an aluminum-to-non-coordinating-anion or Lewis-acid-to-transition-metal molar ratio of about 1:10 to about 20,000:1 or more. The catalyst reacts with the monomer(s) from about −100° C. to about 300° C. for about one second to about 10 hours to produce a polyolefin having from about 1000 or less to about 5,000,000 or more weight average molecular weight and from about 1.5 to about 15 or greater molecular weight distribution.

In another further embodiment, the monoanionic ligand is a substituted phenol joined through an all-carbon bridge to a 6-electron neutral donor ligand. Thus, $H_2C(Me_2tacn)$ ($^tBu_2C_6H_2O)ScCl_2$ (1, $Me_2tacn$=dimethyl triazacyclononane, see figure below) polymerizes ethylene when treated with MAO.

Neutral group three metallocenes ($^RCP_2MX$) tend to dimerize and generally show lower activities than cationic group 4 analogues (e.g. $Cp_2ZrMe^+NCA^-$, NCA=counter anion). Substituting a neutral ligand such as $Me_3tacn$ for Cp would allow the stabilization of isoelectronic group three cationic species (e.g. $Cp(Me_3tacn)jYMe^+NCA^-$) which should be less inclined to dimerize and thus should show more activity. Polyhaptate structures with "hard" donor ligands will be preferred as they may be expected to bind more tightly and be less inclined to be removed by Lewis acids such as trialkyl aluminum scavengers, methylalumoxanes, and $B(C_6F_5)_3$.

The mono-anionic donor ligand E need not be bridged to the neutral donor ligand, nor must it be monohaptate. When it is not bridged to the neutral donor, preferred structures are those that contain steric bulk to help prevent the anionic donor from being removed similarly to the labile ligands. Preferred examples are 2,6-$^iPr_2ArO$—, amidinate ligands, and disubstituted amides.

The neutral polyhaptate ligand L may contain donor "heteroatoms" from groups 15–17 of the periodic table, olefins, alkynes, or neutral carbene groups. The neutral donor may be bidentate, tridentate, tetradentate, or even higher denticity. The donor groups may be linked in a ring as with tacn (triazacyclononane) derivatives, in chains, to a central atom or in a combination thereof. Preferred structures are the triazacyclononanes (9-membered ring), and hexahydrotriazines (6-membered ring). It is expected that different ring sizes will be optimal for different metals and anionic donor ligands. Each linker between heteroatoms or neutral carbon donors need not be of the same composition or length.

The usual ionizing activators known to those skilled in the art may be used for the invention or the compounds may be used without additional activation. Non-coordinating anions comprising perfluoroaryl borates and aluminates are preferred activators since they will not be able to bind the neutral donor atoms of the polyhaptate ligand in a Lewis acid manner as might boranes and neutral aluminum alkyls.

It is clear now that a wide range of molecular weight capability, comonomer incorporation, tacticity control, shear thinning, melt strength, film tear values, and a host of other properties are controlled by variations in catalyst structure and process conditions. To hope to achieve the desired balance of all properties using a given process, a broad selection of catalysts behaviors is essential. It is expected that the catalysts of the invention will provide further tools to achieve these goals.

Definitions

Catalyst system encompasses a catalystprecursor/activator pair. When catalyst system is used to describe such a pair before activation, it means the unactivated catalyst together with the activator. When catalyst system is used to describe such a pair after activation, it means the activated catalyst and the NCA or other charge-balancing moiety.

Cp or cyclopentadienyl encompasses all substituted and unsubstituted ligands in which the 5-carbon-atom, planar aromatic cyclopentadienide ion can be found. This specifically includes fused ring systems in which the 5-carbon ring is fused with other 5-membered rings and fused with 6-and-greater-membered rings. It also specifically includes ligands in which ring carbon atoms are substituted with heteroatoms giving heterocyclic systems. The cyclopentadienyl ligand's 5-member, substantially planar ring should be preserved (heterocyclic or homocyclic), including the π-electrons used to coordinate, side on, to M. Some examples of Cp or cyclopentadienyl are fluorenyl, indenyl, and cyclopentadiene monoanion itself.

Feedstocks are any desired mixture of ethylene, $C_3$–$C_{20}$ α-olefins, $C_4$–$C_{20}$ diolefins, acetylenically unsaturated monomers, or other unsaturated monomers. These feedstocks contain predominately one monomer for homopolymerization; they contain monomer mixtures for copolymerization reactions.

L' is a neutral Lewis base such as, diethyl ether, tetrahydrofuran, dimethylaniline, trimethylphosphine, lithium chloride, or the like, coordinated to the metal-center. It also optionally binds to one or both X, with an appropriate X. L' can also be a second transition metal of the same type as the metal center giving a dimeric catalyst or catalyst precursor, if both of the transition metals are the same or a bimetallic catalyst or catalyst precursor if the transition metals are different.

Monodentate means that a ligand is coordinated to an atom through substantially one, substantially discrete, ligand-atom connection, which is intended to be coextensive with the art recognized meaning.

Bidentate means that a ligand is coordinated to an atom through substantially two, substantially discrete, ligand-atom connections. This definition of bidentate is intended to be coextensive with the art-recognized meaning.

Multidentate means that a ligand is substantially coordinated to an atom through more than one substantially discrete, ligand-atom connection, which is intended to be coextensive with the art recognized meaning.

Noncoordinating anion (NCA) is art recognized to mean an anion that either does not coordinate to the metal cation or that does coordinate to the metal cation, but only weakly enough that a neutral Lewis base, such as an olefinically or acetylenically unsaturated monomer can displace it. Any metal or metalloid that can form a compatible, weakly or negligibly coordinating complex may be used or contained in the noncoordinating anion. Suitable metals include, but are not limited to, aluminum, gold, and platinum. Suitable metalloids include, but are not limited to, boron, phosphorus, and silicon. The description of noncoordinating anions and their precursors in the documents cited in the paragraphs above are incorporated by reference for purposes of U.S. patent practice.

Polymerization encompasses any polymerization reaction such as homopolymerization and copolymerization. It encompasses polymer production including both homopolymers and copolymers with other α-olefin, α-olefinic diolefin, or non-conjugated diolefin monomers, for example $C_3$–$C_{20}$ olefins, $C_4$–$C_{20}$ diolefins, $C_4$–$C_{20}$ cyclic olefins, or $C_8$–$C_{20}$ styrenic olefins. Other olefinically unsaturated monomers besides those specifically described above may be polymerized using the invention catalysts, for example, styrene, alkyl-substituted styrene, ethylidene norbornene, norbornadiene, dicyclopentadiene, vinylcyclohexane, vinylcyclohexene, and other olefinically-unsaturated monomers, including other cyclic olefins, such as cyclopentene, norbornene, and alkyl-substituted norbornenes. Copolymerization can also incorporate α-olefinic macromonomers of up to 1000 or more mer units.

Q are abstractable ligands or leaving groups and olefin insertion ligands connected to the metal center. Usually, activation occurs when one or more Q are removed from the metal. Also, one or more Q remains and as part of the polymerization process, olefin monomer inserts into the metal-center-Q bond. Thus, the Q that remains on the metal center is known as an olefin insertion ligand. Qs independently include, but are not limited to, monoanionic ligands selected from, hydride, hydrocarbyl, alkoxide, aryloxide, amide, or phosphide radicals. Furthermore, both Q together may be an alkylidene, a cyclometallated hydrocarbyl, or any other divalent anionic chelating ligand, or Q can be a diene. Exemplary Q in the formulas are diethyl, propyl, butyl, pentyl, isopentyl, hexyl, isobutyl, heptyl, octyl, nonyl, decyl, cetyl, 2-ethylhexyl, phenyl, benzyl, trimethylsilylmethyl, triethylsilylmethyl and the like, with trimethylsilylmethyl being preferred. Exemplary halogen atoms for Q include chlorine, bromine, fluorine, and iodine, with chlorine being preferred. Exemplary alkoxides and aryloxides for Q are methoxide, phenoxide and substituted phenoxides such as 4-methyl-phenoxide. Exemplary amides for Q are dimethylamide, diethylamide, methylethylamide, di-t-butylamide, diisopropylamide, and the like. Exemplary arylamides are diphenylamide and any other substituted phenylamides. Exemplary phosphides for Q are diphenylphosphide, dicyclohexylphosphide, diethylphosphide, dimethylphosphide, and the like. Exemplary alkylidene radicals for both Q together are methylidene, ethylidene, and propylidene. Exemplary cyclometallated hydrocarbyl radicals for both Q together are propylene, and isomers of butylene, pentylene, hexylene, and octylene. Exemplary dienes for both Q together are 1,3-butadiene, 1,3-pentadiene, 1,4-pentadiene, 1,3-hexadiene, 1,4-hexadiene, 1,5-hexadiene, 2,4-hexadiene, 1,3-butadiene, 2-methyl-1,3-pentadiene, 2-methyl-1,3-hexadiene, and 2,4-hexadiene. Qs can also be simple alkyl ligands substituted with at least one trialkyl silyl group. The most preferred Q is —$CH_2SiMe_3$.

R, R', and R'' encompass:
 (i) $C_1$–$C_{20}$ hydrocarbyl radicals;
 (ii) $C_1$–$C_{20}$ substituted hydrocarbyl radicals in which a halogen atom, amido, phosphido, alkoxy, or aryloxy group or any other radical containing a Lewis acidic or basic functionality replace one or more hydrogen atoms including straight and branched alkyl radicals, cyclic hydrocarbon radicals, alkyl-substituted cyclic hydrocarbon radicals, aromatic radicals, alkyl-substituted aromatic radicals such as trifluoromethyl, dimethylaminomethyl, diphenylphosphinomethyl, methoxymethyl, phenoxyethyl, trimethylsilylmethyl and the like; and
 (iii) $C_1$–$C_{20}$ hydrocarbyl-substituted metalloid radicals wherein the metalloid is a Group-13-14 element such as trimethylsilyl, triethylsilyl, ethyldimethylsilyl, methyldiethylsilyl, triphenylgermyl and the like.

Additionally, any R or R'' may join with one or more R or R'' to form a ring structure. Separately, R'' may also be a hydride radical.

TACN is 1,4,7-triazacyclononane.
TAN is 1,5,9-triazanonane.
TACH is 1,3,5-triazacyclohexane.
DACN is 1,4-diazacyclononane.
TACDD is 1,5,9-triazacyclododecane.
TNNCN is 1,2,6-triazacyclononane.
TNNCH is 1,2,5-triazacycloheptane.
TAH is 1,4,7-triazaheptane.

DETAILED DESCRIPTION

The transition metal complex of the catalyst system of the invention may be represented by the formula:

M is a metal preferably in a +3 oxidation state.

L, optionally T, and E comprise the polyhaptate neutral donor ligand, optional bridge, and anionic ligand; Q (x=0–3) are independently monoanionic ligands selected from halide, hydride, hydrocarbyl, alkoxide, aryloxide, amide or phosphide radicals. For Q of 2 or more, two Q together may be an alkylidene or a cyclometallated hydrocarbyl or any other divalent anionic chelating ligand, or a diene, but may not be a substituted or unsubstituted cyclopentadienyl radical. L' (y=0–3) are donor ligands. It is anticipated that the number of Q may be such that the complex bears a negative charge (i.e. an "ate" complex such as (LTE)ScCl$_3^-$Li$^+$) and still be suitable for the inventive use.

L is a polyhaptate ligand and may contain donor "heteroatoms" from groups 15–17 of the periodic table, olefins, alkynes, B—N pi bonds, or neutral carbene groups such that the atoms bound to M do not contain substantial negative charge. The neutral donor may be bidentate, tridentate, tetradentate, or even higher denticity. The donor groups may be linked in a ring as with tacn (triazacyclononane) derivatives, in chains, to a central atom or in a combination thereof. Preferred structures are the triazacyclononanes (9-membered ring), and hexahydrotriazines (6-membered ring). It is expected that different ring sizes will be optimal for different metals and anionic donor ligands. Each linker between heteroatoms or neutral carbon donors need not be of the same composition or length. L is capable of donating at least four electrons to M. Preferably L contains two, or more preferably three, Group-15 or -16 atoms. In a preferred embodiment, these atoms are nitrogen. A preferred geometry of L is such that it coordinates to the metal through the Group-15 atoms' lone pair electrons reminiscent of $\eta^5$, cyclopentadienyl side-on coordination.

T is an optional covalent bridging group containing at least one Group 13–16 atom. When present, it connects the multihaptate ligand, L, with the anionic ligand, E, and completes a metallocycle fragment, M(LTE). T's chain length influences the geometry of the metallocycle fragment. Examples of T include, but are not limited to, dialkyl, alkylaryl or diaryl, silicon or germanium radicals, alkyl or aryl, phosphine or amine radicals, or hydrocarbyl radicals such as methylene, ethylene, and isopropylene. In a preferred embodiment, the polyhaptate ligand joined to the monoanionic ligand is a substituted phenol joined through an all carbon bridge to the polyhaptate neutral group.

E is an anionic ligand containing at least one group 14–16 element and may be a substituted or unsubstituted, cyclopentadienyl, allyl, or other delocalized pi-anion, a Group-15 ligand such as amide, phosphaimide, or phosphide, or Group-16 ligand such as aryloxide or thiolate.

Preferably when E is not bridged to L it will be branched on the atom bound to M or on the next (beta) atom, or it will be part of a polyhaptate binding group or otherwise sterically protected against substitution. Examples of E include N(SiMe$_3$)$_2$, diisopropylphenyl, —N=PR$_3$, and substituted amidinates.

When E is a substituted cyclopentadienyl ligand, the substitution can occur on the ring, keeping the C$_5$ ring intact (on-ring substitution), or can occur in the ring, creating heterocyclic compounds (in-ring substitution). On-ring substitutions range from simple unitary substitution up to the replacement of multiple hydrogen atoms with multidentate ligands forming fused-ring systems such as in- or on-ring substituted, or unsubstituted, fluorenyl or indenyl ligands. An important characteristic of a cyclopentadienyl ligand is that the 5-member, substantially planar ring be preserved (heterocyclic or homocyclic), including the π-electrons used to coordinate, side on, to M.

Q are independently monoanionic ligands selected from halide, hydride, hydrocarbyl, alkoxide, aryloxide, bridging oxo or sulfide, amide or phosphide radicals. For Q of 2 or more, two Q together may be an alkylidene or a cyclometallated hydrocarbyl or any other divalent anionic chelating ligand, =NH, oxo or sulfido, or a diene, but may not be a substituted or unsubstituted cyclopentadienyl radical.

L' is a neutral Lewis base such as, diethyl ether, tetrahydrofuran, dimethylaniline, trimethylphosphine, lithium chloride, cylcooctene, cyclooctadiene or the like, and optionally covalently binds to one or both X. L' can also be a second transition metal of the same type, i.e. the transition metal component can be dimeric if both of the transition metals are the same or bimetallic if they are different.

In a preferred embodiment the transition metal complex of the catalyst system of the invention is believed to be cationic and may be represented by the formula:

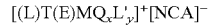

M is a metal preferably in a +3 oxidation state.

The compositions of L, T, E, M, Q, L', x, and y are essentially the same as in the neutral transition metal catalyst above, except that the preferred Q will not be halide, alkoxide, or amide unless the catalyst is used in the presence of a main group alkyl complex such as trialkyl aluminums, alkyl zincs, methyalumoxane, trialkylboron, and the like. NCA is a weakly or non-coordinating anion that balances the positive charge on the transition metal catalyst complex. Non-coordinating anions comprising perfluoroaryl borates and aluminates are preferred activators. It is anticipated that they will not be able to bind the neutral donor atoms of the polyhaptate ligand in a Lewis acid manner.

In a further embodiment, a polymerization process according to the present invention (invention polymerization process), such as the polymerization or copolymerization of olefins, comprises the steps of optionally contacting the transition metal complex of the catalyst system with an activator, optionally contacting the complex with a scavenger, and contacting the transition metal complex with suitable feedstocks.

In a preferred embodiment, a polymerization process according to the present invention (invention polymerization process), such as the polymerization or copolymerization of olefins, comprises the steps of activating (ionizing) the Group 3 or Lanthamide metal component to a cation (the catalyst) and contacting it with suitable feedstocks.

Those skilled in the art will recognize that some forms of the transition metal complex of the catalyst system will not require an activator e.g. certain cationic compositions or neutral compositions directly competent for polymerization of olefins. Additionally it will be recognized that certain compositions of the transition metal complex of the catalyst system in low oxidation states (e.g. less than 3+) will be capable of olefin polymerization upon contact with activators or scavengers. For example where L' or Q are dienes which can be formally considered neutral or dianionic ligands, those skilled in the art will understand that polymerization activity may be observed directly upon contact with olefin or after treatment with activator and/or scavenger. Likewise where L' is cyclooctene or cyclooctadiene, protonation of the bound olefin will result in the creation of a cationic metal-alkyl complex which is formally two oxidation states higher than the precursor complex and may be competent for polymerization.

These feedstocks contain predominately one monomer for homopolymerization; they contain monomer mixtures for copolymerization. Suitable feedstocks are made up of any desired mixture of ethylene, C$_3$–C$_{20}$ α-olefins, C$_5$–C$_{20}$ diolefins, acetylenically unsaturated monomers, or other unsaturated monomers. The catalyst can optionally be dissolved, suspended, or fluidized in a suitable liquid or gaseous polymerization diluent. The catalyst is activated with alumoxanes, modified alumoxanes, non-coordinating anion activators, Lewis acids or the like, (alone or in combination), with an aluminum-to-non-coordinating-anion or Lewis-acid-to-transition-metal molar ratio of about 1:10 to about 20,000:1 or more. The catalyst reacts with the monomer(s) from about −100° C. to about 300° C. for about one second to about 10 hours to produce a polyolefin having from about 1000 or less to about 5,000,000 or more weight average molecular weight and from about 1.5 to about 15 or greater molecular weight distribution.

In another embodiment, the metal complex is represented by the following formula:

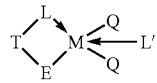

(A)

M is a metal in a +3 oxidation state.

LTE is a multidentate ligand; Q are independently monoanionic ligands selected from halide, hydride, hydrocarbyl, alkoxide, aryloxide, amide or phosphide radicals. Both Q together may be an alkylidene or a cyclometallated hydrocarbyl or any other divalent anionic chelating ligand, or a diene, but may not be a substituted or unsubstituted cyclopentadienyl radical.

L is a bulky, neutral multidentate ligand containing at least two, preferably three, Group-15 or -16 atoms. In a preferred embodiment, these atoms are nitrogen. The geometry of L is such that it coordinates to the metal through the Group-15 atoms' lone pair electrons. Ligand geometry orients the lone pair electrons so that they overlap the metal's frontier d-orbitals, reminiscent of $\eta^5$, cyclopentadienyl side-on coordination.

T is an optional covalent bridging group containing at least one Group 13–16 atom. When present, it connects the multidentate ligand, L, with the anionic ligand, E, and completes a metallocycle fragment, M(LTE). T's chain length influences the geometry of the metallocycle fragment. Examples of T include, but are not limited to, dialkyl, alkylaryl or diaryl, silicon or germanium radicals, alkyl or aryl, phosphine or amine radicals, or hydrocarbyl radicals such as methylene, ethylene, and isopropylene.

E is an anionic ligand containing at least one group 14–16 element and may be a substituted or unsubstituted, cyclopentadienyl, Group-15 ligand such as nitrogen or phosphorus, or Group-16 element such as oxygen or sulfur.

When E is a substituted cyclopentadienyl ligand, the substitution can occur on the ring, keeping the $C_5$ ring intact (on-ring substitution), or can occur in the ring, creating heterocyclic compounds (in-ring substitution). On-ring substitutions range from simple unitary substitution up to the replacement of multiple hydrogen atoms with multidentate ligands forming fused-ring systems such as in- or on-ring substituted, or unsubstituted, fluorenyl or indenyl ligands. An important characteristic of a cyclopentadienyl ligand is that the 5-member, substantially planar ring be preserved (heterocyclic or homocyclic), including the π-electrons used to coordinate, side on, to M.

L' is a neutral Lewis base such as, diethyl ether, tetrahydrofuran, dimethylaniline, trimethylphosphine, lithium chloride or the like, and optionally covalently binds to one or both X. L' can also be a second transition metal of the same type, i.e. the transition metal component can be dimeric if both of the transition metals are the same or bimetallic if they are different.

In cationic form as activated for olefin polymerization, the transition metal complex is believed to have the following formula:

(B)

M, T, E, L, Q and L' are as defined above and NCA is a weakly coordinating or noncoordinating anion that balances the cationic complex's charge.

In yet another embodiment, the transition metal component of the catalyst system has the formula:

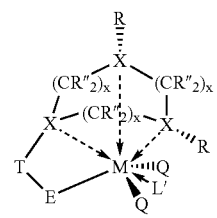

(C)

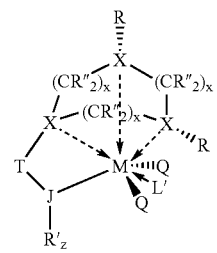

(D)

M, T, E, L, Q and C' are as defined above.

Alternatively, as in structure D, E is $JR'_z$. J is a Group 15 or 16 element; z is 2 when J is a Group 15 element and 1 when J is a Group 16 element. R, R' and R" are defined below.

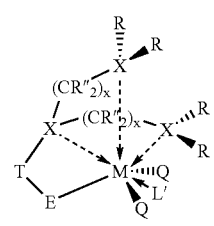

(E)

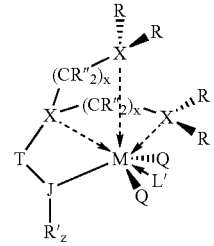

(F)

In yet another embodiment, the multidentate ligand is joined to the monoanionic ligand through a substituted phenol joined forming an all-carbon bridge to the multidentate neutral portion of the ligand.

The structures shown below represent examples of ligand and/or catalyst precursor that are within the scope of this invention. This list does not define the full scope of the invention but rather is exemplary only.
A
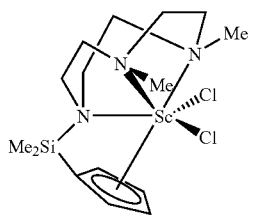
B
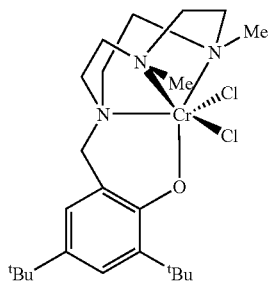
C
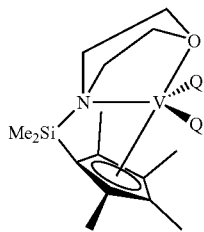
D
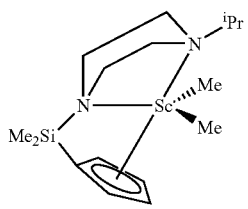
E
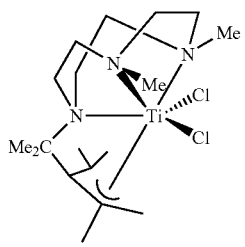
F
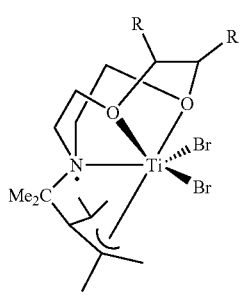
-continued
G
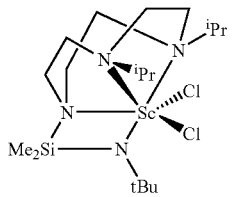
H
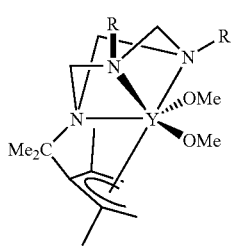
I
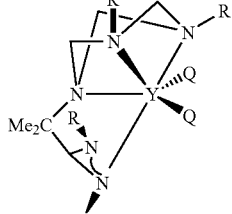
J
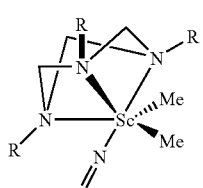
K
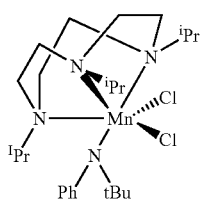
L
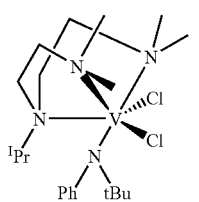
M
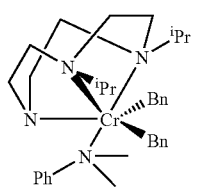

-continued

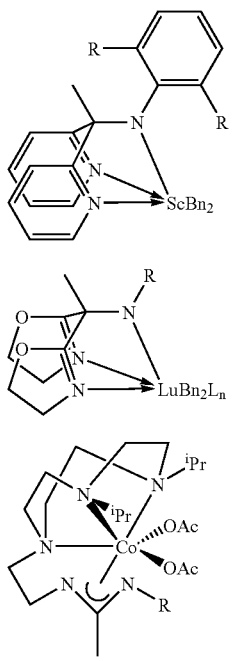

The metal complexes according to this invention can be prepared by various conventional routes.

The metal complexes (catalyst precursors) according to the invention are suitable for polymerization when activated by methods known in the metallocene art. Suitable activators typically include alumoxane compounds, modified alumoxane compounds, and ionizing anion precursor compounds that abstract one reactive, σ-bound metal ligand making the metal complex cationic and providing a charge-balancing noncoordinating or weakly coordinating anion.

Alkylalumoxanes and modified alkylalumoxanes are suitable as catalyst activators, particularly when the abstractable ligand is a halide. Alumoxane components useful as a catalyst activator are typically oligomeric aluminum compounds represented by the general formula $(R^2—Al—O)_m$, (cyclic) or $R^3(R^4—Al—O)_m AlR^5$ (linear), although other structural variations may exist. In a general alumoxane formula, each $R^2$–$R^5$ is independently a $C_1$ to $C_{20}$ hydrocarbyl radical, for example, methyl, ethyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, and m is an integer from 1 to about 50. Most preferably, $R^2$–$R^5$ is methyl and m is at least 4. If an alkyl aluminum halide is used in the alumoxane preparation, $R^2$–$R^5$ can also be halides. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a linear and cyclic alumoxane mixture. Modified and unmodified methylalumoxanes are preferred. Mixtures of different alumoxanes and modified alumoxanes may also be used. For further descriptions, see U.S. Pat. Nos. 4,665,208, 4,952, 540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0279586B1, EP 0516476A, EP 0594218A1 and WO 94/10180.

When the activator is an alumoxane, the minimum metal-complex-to-activator molar ratio is equal to about 1:5000, preferably about 1:500 and most preferably about 1:100. The maximum metal complex to activator molar ratio is about 1:1 and most preferably about 1:10.

The term "noncoordinating anion" is recognized to mean an anion, as represented by the symbol NCA above, which either does not coordinate to the metal cation or that does coordinate to the metal cation, but only weakly enough that a neutral Lewis base, such as an olefinically or acetylenically unsaturated monomer can displace it.

Descriptions of ionic catalysts with a transition-metal cationic complex and a noncoordinating anion, suitable for polymerization appear in U.S. Pat. Nos. 5,064,802, 5,132, 380, 5,198,401, 5,278,119, 5,321,106, 5,347,024, 5,408,017, 5,599,671, and WO 92/00333 and WO 93/14132. These teach a preferred preparation method in which metallocenes are protonated by noncoordinating anion precursors such that an alkyl or hydride group is abstracted from the transition metal compound making it both cationic and charge-balanced by the noncoordinating anion. Since similar ligands may be present in this invention's metal compounds, similar polymerization catalyst activation methods may be followed. Benzyl is a preferred abstractable hydrocarbyl radical.

Using ionic compounds lacking an active proton, but capable of producing both an active metal cationic complex and a noncoordinating anion, is also possible. See, EP-A-0 426 637, EP-A-0 573 403 and U.S. Pat. No. 5,387,568 for illustrative ionic compounds. Reactive cations of the ionic compounds, other than the Bronsted acids, include ferrocenium, silver, tropylium, triphenylcarbenium and triethylsilylium, and alkali and alkaline earth metal cations such as sodium, magnesium or lithium cations. A further class of suitable noncoordinating anion precursors are hydrated salts comprising alkali or alkaline-earth metal cations and a non-coordinating anion as described above. The hydrated salts are made by reacting the metal-cation-noncoordinating-anion salt with water, for example, by hydrolysis of the commercially available or readily synthesized $[Li]^+[B(pfp)_4]^-$, which yields $[Li(H_2O)_x]^+[B(pfp)_4]^-$: pfp is pentafluorophenyl or perfluorophenyl.

Any metal or metalloid that can form a compatible, weakly or negligibly coordinating complex may be used or contained in the noncoordinating anion. Suitable metals include, but are not limited to, aluminum, gold and platinum. Suitable metalloids include, but are not limited to, boron, phosphorus and silicon. The description of noncoordinating anions and their precursors in the documents cited in the paragraphs above are incorporated by reference for purposes of U.S. patent practice.

An additional method of making this invention's active polymerization catalysts uses ionizing-anion precursors that are initially neutral Lewis acids but form a cationic metal complex and a noncoordinating anion, or a Zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of Zwitterionic complexes using analogous Group 4 compounds see U.S. Pat. Nos. 5,624,878; 5,486, 632; and 5,527,929. The description of noncoordinating anions and their precursors in these documents are incorporated by reference for purposes of U.S. Patent practice.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the transition-metal-to-activator molar ratio may be any ratio. While the molar ratio may take any value, the minimum is preferably about 1:10, more preferably about 1:5, even more preferably about 1:12. The maximum transition-metal-to-activator molar ratio is preferably about 10:1, more preferably about 5:1, even more preferably about 1.2:1. The most preferred, transition-metal-to-activator molar ratio is 1:1. Combinations of the described activator compounds may also be used for activation. For example, tris(perfluorophenyl) boron can be used in conjunction with methylalumoxane.

The invention's catalyst complexes are useful in polymerizing unsaturated monomers conventionally known to undergo metallocene-catalyzed, coordination polymerization such as solution polymerization, slurry polymerization, gas-phase polymerization, and high-pressure polymerization. These catalysts may be supported and as such will be particularly useful in the known, fixed-bed, moving-bed, fluid-bed, slurry, or solution operating modes conducted in single, series, or parallel reactors.

Generally, when using this invention's catalysts, particularly when they are immobilized on a support, the complete catalyst system will additionally comprise one or more scavenging compounds. Here, the term "scavenging compounds" means compounds that remove polar impurities from the reaction environment. Impurities can be inadvertently introduced with any of the polymerization reaction components, particularly with the solvent, monomer and catalyst feeds.

These impurities adversely affect catalyst activity and stability. They diminish or eliminate catalytic activity, particularly when ionizing anion precursors activate the catalyst system. Polar impurities, or catalyst poisons include water, oxygen, metal impurities, etc. Preferably, purifying steps occur before introducing reaction components to the reaction vessel. Such steps include chemical treatment or careful separation during or after the various components' synthesis or preparation. But such steps will rarely allow polymerization without using some scavenging compounds. Normally, the polymerization process will still use at least small amounts of scavenging compounds.

Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, isobutyl aluminumoxane, and tri-n-octyl aluminum. Those scavenging compounds having bulky or $C_6$–$C_{20}$ linear hydrocarbyl substituents covalently bound to the metal or metalloid center are preferred to minimize adverse interaction with the active catalyst. Examples include triethylaluminum, but more preferably, bulky compounds such as triisobutylaluminum, triisoprenylaluminum, and long-chain linear alkyl-substituted aluminum compounds, such as tri-n-hexylaluminum, tri-n-octylaluminum, or tri-n-dodecylaluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$. In this invention, only enough scavenging agent is used to enhance activity: pure enough feeds avoid scavenging agent altogether.

The invention catalysts can be supported for gas-phase, bulk, or slurry polymerization use, or otherwise as needed. Numerous support methods are known for catalysts in the olefin copolymerization art, particularly alumoxane-activated catalysts; any are suitable for this invention's broadest practice. See, for example, U.S. Pat. Nos. 5,057,475 and 5,227,440. An example of supported ionic catalysts appears in WO 94/03056. U.S. Pat. No. 5,643,847 and WO 96/04319A describe a particularly effective method. A bulk or slurry process using this invention's supported metal complexes activated with alumoxane can be used for ethylene-propylene rubber as described in U.S. Pat. Nos. 5,001,205 and 5,229,478. Additionally, those processes suit this invention's catalyst systems. Both polymers and inorganic oxides may serve as supports, as is known in the art. See U.S. Pat. Nos. 5,422,325, 5,427,991, 5,498,582 and 5,466,649, and international publications WO 93/11172 and WO 94/07928. All of these documents are incorporated by reference for purposes of U.S. patent practice.

Preferred embodiments employ the catalyst system in the liquid phase (solution, slurry, suspension, bulk phase, or suitable combinations), in high-pressure, liquid or supercritical fluid phases, or in the gas phase. Each may be employed in singular, parallel, or series reactors. The liquid processes comprise contacting olefin monomers with the catalyst system described above. The reaction is carried out in a suitable diluent or solvent for a time sufficient to produce this invention's copolymers. Both aliphatic and aromatic hydrocarbyl solvents are suitable; hexane and toluene are preferred. Typically, in bulk and slurry processes, the liquid monomer slurry contacts the supported catalysts. Gas-phase processes typically use a supported catalyst and are conducted in any suitable manner for ethylene homo- or copolymerization. Illustrative examples may be found in U.S. Pat. Nos. 4,543,399, 4,588,790, 5,028,670, 5,382,638, 5352,749, 5,436,304, 5,453,471, and 5,463,999, and WO 95/07942. Each is incorporated by reference for purposes of U.S. patent practice.

Polymerization reaction temperatures can vary. The minimum reaction temperature is about –50° C.; preferably the minimum is about –20° C. The maximum temperature is about 250° C. preferably at or below about 220° C. Most preferably, the reaction temperature will be at or below about 200° C.

Linear polyethylene, including high- and ultra-high-molecular-weight polyethylenes are produced by adding ethylene, and optionally one or more other monomers, to a reaction vessel with an invention catalyst. The polymers can include both homopolymers and copolymers with other α-olefin, α-olefinic diolefin, or non-conjugated diolefin monomers, for example $C_3$–$C_{20}$ olefins, $C_4$–$C_{20}$ diolefins, $C_4$–$C_{20}$ cyclic olefins, or $C_8$–$C_{20}$ styrenic olefins. The invention catalyst is first slurried with or dissolved in a solvent, such as hexane or toluene. Most often, cooling removes polymerization heat. Gas-phase polymerization can be conducted, for example, in a continuous, fluidized-bed, gas-phase reactor operated between about 200–3000 kPa and at about 60–160° C., using hydrogen as a reaction modifier (100–200 ppm), a $C_4$–$C_8$ comonomer feedstream (0.5–12 mol %), and a $C_2$ feedstream (25–35 mol %). See, U.S. Pat. Nos. 4,543,399; 4,588,790; 5,028,670; 5,405,922; and 5,462,999, which are incorporated by reference for purposes of U.S. patent practice.

Ethylene-α-olefin (including ethylene-cyclic olefin and ethylene-α-olefin-diolefin) elastomers of high molecular weight and low crystallinity can be prepared using the invention catalysts under traditional solution polymerization conditions or by introducing ethylene gas into a slurry of polymerization diluent and catalyst. The polymerization diluent contains α-olefin monomers, cyclic olefin monomers, or their mixtures with other polymerizable and non-polymerizable monomers. In this case, polymerization reaction pressure varies, as well. The minimum pressure is about 0.0013 bar; a pressure of at least about 0.1 bar is more preferred. Most preferably, the reaction pressure is at least about 1.0 bar. The maximum pressure is about 2500 bar, with a pressure at most about 1600 bar being preferred. The most preferred maximum pressure is about 500 bar. Typical ethylene pressures will be between 10 and 1000 psig (69–6895 kPa) and the polymerization diluent temperature will typically be between −10 and 160° C. The process can use a stirred-tank reactor, or more than one reactor operated in series or parallel. See the general disclosure of U.S. Pat. No. 5,001,205, which is incorporated by reference for its description of polymerization processes, ionic activators and useful scavenging compounds.

Slurry or gas-phase reaction processes can use pre-polymerization of the supported invention catalyst to further control polymer particle morphology, as is known in the art. For example, such reaction can be accomplished by prepolymerizing a $C_2$–$C_6$ α-olefin for a limited time. Ethylene contacts the supported catalyst at between −15° to 30° C. and ethylene pressure of up to about 250 psig (1724 kPa) for 75 min to obtain a polyethylene coating on the support (30,000–150,000 molecular weight). The above polymerization process can then use the pre-polymerized catalyst. Additionally, polymeric resins may be used as a support coating, typically by suspending a support in dissolved polystyrene resin or similar material followed by separation and drying.

Other olefinically unsaturated monomers besides those specifically described above may be polymerized using the invention catalysts, for example, styrene, alkyl-substituted styrene, ethylidene norbornene, norbornadiene, dicyclopentadiene, vinylcyclohexane, vinylcyclohexene, and other olefinically-unsaturated monomers, including other cyclic olefins, such as cyclopentene, norbornene, and alkyl-substituted norbornenes. Copolymerization can also incorporate α-olefinic macromonomers of up to 1000 or more mer units.

The invention catalyst compositions can be used individually as described above or can be mixed with other known polymerization catalysts to prepare polymer blends. Monomer and catalyst selection allows polymer blend preparation under conditions analogous to those using individual catalysts. Polymers having increased MWD for improved processing and other traditional benefits available from polymers made with mixed catalyst systems can thus be achieved.

EXAMPLES

The following examples are presented to illustrate the discussion above. Although the examples may be directed toward certain embodiments of the present invention, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, and THF=tetrahydrofuran.

All parts, proportions, and percentages are by weights unless otherwise indicated. All molecular weights are weight average molecular weight unless otherwise noted. Molecular weights (weight average molecular weight (Mw) and number average molecular weight (Mn)) were measured by Gel Permeation Chromatography, unless otherwise noted, using a Waters 150 Gel Permeation Chromatograph equipped with a differential refractive index detector and calibrated using polystyrene standards. Samples were run in either THF (45° C.) or in 1,2,4-trichlorobenzene (145° C.), depending upon the sample's solubility, using three Shodex GPC AT-80 M/S columns in series. This general technique is discussed in "Liquid Chromatography of Polymers and Related Materials III" J. Cazes Ed., Marcel Decker, 1981, page 207, which is incorporated by reference for purposes of U.S. patent practice. No column spreading corrections were employed but data on generally accepted standards, e.g. National Bureau of Standards Polyethylene 1475, demonstrated a precision with 0.1 units for $M_w/M_n$, which was calculated from elution times. Numerical analyses were performed using Expert Ease® software available from Waters Corporation. The term "psid" refers to the differential pressure resulting from monomer addition.

All preparations were performed under an inert nitrogen atmosphere, using standard Schlenk or glovebox techniques, unless mentioned otherwise. Dry solvents were purchased from Aldrich in anhydrous, air-free form and were degassed and vacuum transferred from sodium/benzophenone (THF, diethyl ether) phosphorus pentoxide (methylene chloride) or $CaH_2$ (pentane) before use. If these additional steps were not taken some compounds were observed to form insoluble light ppt.s upon handling in solution. The toluene used in the polymerization experiments (high purity from ExxonMobil Chemical Co.) was passed through columns of supported reduced copper scavenger and molecular sieves (Oxyclear) and activated alumina (basic, Brockmann 1). Ethylene (high purity from ExxonMobil Chemical Co.) was likewise purified. Hexene obtained anhydrous and air-free was further sparged with nitrogen. Deuterated solvents were degassed and vacuum transferred from sodium/benzophenone (THF) or $CaH_2$ (benzene, toluene, $C_6D_5Br$, methylene chloride) before use. $ScCl_3$ was purchased from Aldrich and $YCl_3$ from Strem, while $Y(CH_2SiMe_3)_3(THF)_n$ (n~2.3) was prepared according to the method of Lappert and Pearce (*J. C. S. Chem. Comm.* (1973) 126). The ligands $R_2$tacn-6-$CH_2$—Ar-1-OH ($L^2$ R=Me, Ar=2,4-$^tBu_2$; $L^3$ R=$^i$Pr, Ar=2,4-$Me_2$) were purchased from an outside supplier and can be made according to the method of Tolman et al. (*J. Am. Chem. Soc.*, 119 (1997) 8217). Triethylhexahydrotriazine, $Et_3$htz (1,3,5-triethyl-[1,3,5]triazacyclohexane), was purchased from Aldrich (drid over $CaH_2$ and filtered). The parent triazacyclononane, triaza[1,4,7]cyclononane was purchased from Aldrich or Macrocyclics. The trimethyl derivative 1,4,7-trimethyl-triaza[1,4,7]cyclononane was made by treating the parent macrocycle with formaldehyde in formic acid as described by Wiegahardt et al. (*Inorg. Chem.*, 21 (1982) 3086). The potassium salt of 2,6-diisopropylphenol (2,6-$^iPr_2C_6H_3OK$) was made by treating the phenol with excess KH in THF.

Example Ligand 1

Synthesis of $L^2K$ ($Me_2$tacn-6-$CH_2$-2,4-$^tBu_2$-$C_6H_3$-1-OK).

To 0.208 g $Me_2$tacn-6-$CH_2$-2,4-$^tBu_2$-$C_6H_3$-1-OH in 25 mL of THF was slowly added 0.029 g of KH causing gas evolution. About 0.060 g more KH was likewise added. After stirring over night the orange-brown solution was filtered via Celite, washed with THF and the solvent removed under vacuum. The residue was stirred with pentane which was stripped. Attempted recrystallization at −35 C yielded ppt.s but not crystals so the solvent was stripped affording 0.177 g (77% yield) of orange-brown material which was determined to be the desired product by $^1$H-NMR analysis.

Example Catalyst 1

Synthesis of $L^2ScCl_2$ (($Me_2tacn$-6-$CH_2$-2,4-$^tBu_2$-$C_6H_3$-1-O)$ScCl_2$).

$ScCl_3$, 0.066 g, was added to 50 mL refluxing THF, refluxed about 25 min, and removed from the heat. The entire sample of $L^2K$ from the previous example that had been taken up in about 1 mL of THF-$d_8$ was diluted with about 20 mL of THF and slowly added dropwise to the $ScCl_3$ solution with stirring. The next day an aliquot was removed for $^1$H-NMR analysis and the remainder stripped under vacuum. The residue was extracted with methylene chloride, filtered on a medium frit to remove red-brown solids, and the filtrate stripped to dryness to yield 0.142 g (70% yield) of light solids whose $^1$H-NMR was consistent with the desired structure.

Example Catalyst 2

Synthesis of $Me_3tacn(ArO)ScCl_2$ (Ar=2,6-$^iPr_2Ph$).

$ScCl_3$, 0.350 g, was added to 50 mL refluxing THF, refluxed about 25 min, and removed from the heat. After cooling, 0.410 g of $Me_3tacn$ was added followed by 0.502 g of solid 2,6-$^iPr_2$PhOK causing a transient lavender coloration. After stirring overnight white flocculent precipitates were observed. The solvent was removed under vacuum and the solids were triturated with methylene chloride which was removed under vacuum. The solids were triturated unintentionally with THF which was removed under vacuum and the methylene chloride trituration repeated. The residues were then extracted into methylene chloride and the mixture filtered on a medium porosity frit, washed with methylene chloride, and the filtrate reduced to dryness under vacuum to yield 0.784 g of a yellow-white powder (73% yield) whose $^1$H-NMR was consistent with the desired structure.

Example Catalyst 3

Synthesis $Et_3htz(ArO)ScCl_2$ (Ar=2,6-$^iPr_2Ph$).

$ScCl_3$, 0.350 g, was added to 50 mL refluxing THF, refluxed about 25 min, and removed from the heat. After cooling, 0.412 g of $Et_3htz$ (triethylhexahydrotriazine) was added followed by 0.509 g of solid 2,6-$^iPr_2$PhOK. After stirring the solution appeared milky. The solvent was removed under vacuum and the solids were triturated with methylene chloride which was removed under vacuum. The residues were then extracted into methylene chloride and the mixture filtered on a medium porosity frit, washed with methylene chloride, and the filtrate reduced to dryness under vacuum to yield 0.780 g of a white powder (73% yield) whose 1H-NMR was consistent with the desired structure.

Example Catalyst 4

Synthesis of $L^1Y(CH_2SiMe_3)_2$ (($^iPr_2tacn$-6-$CH_2$-2,4-$^tBu_2$-$C_6H_3$-1-O) $Y(CH_2SiMe_3)_2$).

A −35 C solution of 0.204 g $L^1H$ in 5–10 mL of toluene was added drop-wise into a −35 C solution of 0.239 g $Y(CH_2SiMe_3)_3(THF)_{2.3}$ in 5–10 mL of toluene. After warming 2 hr the solvent was removed under vacuum. The solids were triturated with several mL of pentane and cooled to −35 C. The precipitates were collected by filtration and dried under vacuum affording 0.223 g white solids (69% yield) whose $^1$H-NMR was consistent with the desired structure.

Example Polymerization 1

Vial Polymerization with $L^2ScCl_2$.

In a vial polymerization test, a 20 mL vial was filled with 0.002 g of (##), 10 mL toluene, 1.58 g 30 wt % Albemarle MAO, and a stir bar. A septum was fitted on the top and 1 atm ethylene purged through the headspace. After stirring, solids appeared. After 45 minutes, the solution was quenched with methanol and then stirred with 25 mL 1 N HCl, then 12 mL 4 N HCl to dissolve the aluminum oxides. The sample was filtered, washed with water and dried under vacuum at 80° C. overnight. The amount collected from the filter paper was 0.007 g.

Example Polymerization 2

Autoclave Polymerization with EXAMPLE CATALYST 1 ($L^2ScCl_2$)

A 2 L Zipperclave reactor was charged with 800 mL toluene and 1 mL of 10 wt. % Albemarle MAO and warmed to 60° C. Next, 0.0050 g of 1 was weighed out and treated with 2 mL of 10 wt. % Albemarle MAO with stirring. This solution was injected into the reactor which was then pressurized with 75 psid of ethylene and stirred at 800–1000 rpm. After 60 minutes, the reactor was opened, the material poured into isopropanol, treated with acidified methanol, and the solvent weathered off under a stream of air. This material was stirred with fresh acidifed methanol, filtered, washed with water, and dried under vacuum at 80° C. overnight to yield 0.306 g of white polyethylene.

Example Polymerizations 3

These polymerizations were performed according to the procedure of Example Polymerization 2, and the materials and amounts that were different are recorded in Table 1. Blank runs in which either no transition metal complex or no methylalumoxane were added to the reactor were performed and indicated the necessity of having both components present for significant polymerization activity.

TABLE 1

MAO Polymerization Data

| Ex. | Catalyst | Cat. mmols | MAO wi. catalyst mmols | MAO in. reactor mmols | Al/M | Hexene mL | Run t min | Yield g | Specific Activity gPE/mmol M atm hr |
|---|---|---|---|---|---|---|---|---|---|
| 2 | $L_2ScCl_2$ | 0.01081 | 3.06467 | 1.53234 | 425.1 | 0 | 60 | 0.306 | 5.547 |
| 3C | none | 0.00000 | NA | 4.59701 | NA | 0 | 30 | 0.036 | §0.003 |
| 4 | $L_2ScCl_2$ | 0.01081 | 3.06467 | 1.53234 | 425.1 | 90 | 30 | 0.210 | 7.613 |
| 5 | $L_2ScCl_2$ | 0.01081 | 3.06467 | 1.53234 | 425.1 | 90 | 60 | 0.600 | 10.876 |
| 6 | $Et_3htzDIPScCl_2$ | 0.01077 | 3.06467 | 1.53234 | 427.0 | 0 | 60 | 0.890 | 16.202 |
| 7C | none | 0.00000 | NA | 4.59701 | NA | 0 | 30 | 0.049 | §0.004 |

TABLE 1-continued

MAO Polymerization Data

| Ex. | Catalyst | Cat. mmols | MAO wi. catalyst mmols | MAO in. reactor mmols | Al/M | Hexene mL | Run t min | Yield g | Specific Activity gPE/mmol M atm hr |
|---|---|---|---|---|---|---|---|---|---|
| 8C | L$_2$ScCl$_2$* | 0.01081 | 0.00000 | 0.00000 | 0.0 | 0 | 30 | 0.000 | 0.000 |
| 9 | Et$_3$htzDIPScCl$_2$ | 0.01077 | 3.06467 | 1.53234 | 427.0 | 90 | 60' | 0.710 | 12.925 |

*This comparative run contained 0.050 mL of 25 wt% TEAL in heptane (Akzo) as scavenger.
§Here the mmoles Al are used for mmoles M.

Example Polymerization 9

Autoclave Polymerization with EXAMPLE CATALYST 4 (L$^1$Y(CH$_2$SiMe$_3$)$_2$)

Initial polymerization attempts under the conditions of example polymerization 2 except that 5 mg charges of Catalyst 4 in 5 mL toluene added into a reactor containing 2 mL 10 wt. % MAO yielded about 0.2 g or less of polymer. Similarly, adding 5 mL of a solution made from 6 mg Catalyst 4 and 7 mg dimethylanilinium tetrakispentafluorophenylborate in 12 mL toluene, into a reactor with 0.050 mL triisobutyl aluminum (25 wt. % in toluene) yielded negligible amounts of polymer. We believe the substitution of a smaller alkyl group on yttrium would improve polymerization performance.

The invention claimed is:

1. An olefin polymerization process comprising:
   (a) providing monomer;
   (b) providing a polymerization catalyst comprising:
      (i) a Group -7, -8 or -9 metal in a +3 oxidation state;
      (ii) a multidentate ligand comprising:
         (iii) a subpart comprising at least three Group-15 moieties, each bridged to another through at least one Group-14 moiety wherein the subpart connects to the metal and wherein each Group-15 moiety is optionally bonded to a substituted or unsubstituted organic group;
         (iv) a monoanion connected to the metal, wherein the monoanion is other than cyclopentadienyl; and
         (v) a bridge that connects the monoanion to the subpart;
   (c) contacting the monomer with the catalyst under suitable polymerization conditions.

2. The process of claim 1 wherein the subpart contains a ring comprising at least two of the Group-15 moieties.

3. The process of claim 1 wherein the multidentate ligand contains a ring comprising at least three Group-15 moieties.

4. The process of claim 1 wherein the bridge comprises at least one Group-13-to-16 element.

5. An olefin polymerization process comprising:
   (a) providing monomer;
   (b) providing a polymerization catalyst precursor comprising:
      (i) a Group -7, -8 or -9 metal in a +3 oxidation state;
      (ii) a multidentate ligand comprising:
         (A). a subpart comprising at least three Group-15 moieties, each bridged to another through at least one Group-14 moiety wherein the subpart connects to the metal and wherein each Group-15 moiety is optionally bonded to a substituted or unsubstituted organic group;
         (B) a monoanion connected to the metal, wherein the monoanion other than cyclopentadienyl; and
         (C) a bridge that connects the monoanion to the subpart;
   (c) providing an activator,
   (d) activating the catalyst precursor with the activator, end
   (e) contacting the monomer with the activated catalyst under suitable polymerization conditions.

6. A catalyst comprising an activator and a metal complex wherein the metal complex has the following formula

wherein
   (a) M is a +3 oxidation state Group-4 to -9 metal;
   (b) X are abstractable ligands
   (c) R is selected from
      (i) C$_1$–C$_{20}$ hydrocarbyl radicals;
      (ii) C$_1$–C$_{20}$—substituted hydrocarbyl radicals having at least one hydrogen group wherein one of the at least one hydrogen groups is substituted by a halogen; amido; phosphido; alkoxy; or aryloxy group; and
      (iii) C$_1$–C$_{20}$ hydrocarbyl-substituted Group-13–14 metalloid radicals;
   (d) T is a covalent bridging group comprising at least one Group-14 or -15 atom;
   (e) R' is selected from
      (iv) Halide;
      (v) C$_1$–C$_{20}$ hydrocarbyl radicals;
      (vi) C$_1$–C$_{20}$—substituted hydrocarbyl radicals having at least one hydrogen group wherein one of the at least one hydrogen groups is substituted by a halogen; amido; phosphido; alkoxy; or aryloxy group; and
      (vii) C$_1$–C$_{20}$ hydrocarbyl-substituted Group-13–14 metalloid radicals;
   (f) L' is a neutral Lewis base.

7. A catalyst comprising an activator and a metal complex with the following formula

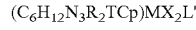

wherein
   (a) M is a +3 oxidation state Group-4 to -9 metal;
   (b) X are abstractable ligands;
   (c) each R are independently selected from
      (i) C$_1$–C$_{20}$ hydrocarbyl radicals;
      (ii) C$_1$–C$_{20}$—substituted hydrocarbyl radicals having at least one hydrogen group wherein one of the at least one hydrogen groups is substituted by a halogen; amido; phosphido; alkoxy or aryloxy group; and
      (iii) C$_1$–C$_{20}$ hydrocarbyl-substituted Group-13–14 metalloid radicals;
   (d) T is a covalent bridging group comprising at least one Group-14 or -15 atom;
   (e) L' is a neutral Lewis base; and
   (f) Cp is a cyclopentadienyl ligand.

* * * * *